(12) United States Patent
Ganjvar

(10) Patent No.: US 11,559,799 B2
(45) Date of Patent: Jan. 24, 2023

(54) REMOVABLE IMPINGEMENT BASKET FOR ETHYLENE OXIDE (EO) REACTORS

(71) Applicant: Scientific Design Company, Inc., Little Ferry, NJ (US)

(72) Inventor: Mohammad Ganjvar, Mahwah, NJ (US)

(73) Assignee: Scientific Design Company, Inc., Little Ferry, NJ (US)

( * ) Notice: Subject to any disclaimer, the term of this patent is extended or adjusted under 35 U.S.C. 154(b) by 107 days.

(21) Appl. No.: 17/130,961

(22) Filed: Dec. 22, 2020

(65) Prior Publication Data
US 2022/0193650 A1 Jun. 23, 2022

(51) Int. Cl.
| | |
|---|---|
| *B01J 8/06* | (2006.01) |
| *C07D 301/10* | (2006.01) |
| *B01J 37/02* | (2006.01) |
| *B01J 23/50* | (2006.01) |
| *B01J 37/08* | (2006.01) |

(52) U.S. Cl.
CPC .......... *B01J 37/0201* (2013.01); *B01J 8/065* (2013.01); *B01J 23/50* (2013.01); *C07D 301/10* (2013.01); *B01J 37/08* (2013.01); *B01J 2204/00* (2013.01); *B01J 2208/0092* (2013.01); *B01J 2208/00938* (2013.01); *B01J 2208/06* (2013.01)

(58) Field of Classification Search
None
See application file for complete search history.

(56) References Cited

U.S. PATENT DOCUMENTS

| | | | | | |
|---|---|---|---|---|---|
| 943,461 | A | * | 12/1909 | Reynolds | F16L 23/032 285/368 |
| 2,440,436 | A | * | 4/1948 | Creel | B01J 8/0278 422/220 |
| 3,363,843 | A | * | 1/1968 | Ballard | B01D 3/008 261/97 |
| 3,479,146 | A | * | 11/1969 | Hochman | B01J 8/0278 422/220 |
| 3,547,354 | A | * | 12/1970 | Greathouse | B01J 8/0278 239/522 |
| 3,563,914 | A | | 2/1971 | Wattimena | |

(Continued)

FOREIGN PATENT DOCUMENTS

| | | | |
|---|---|---|---|
| CN | 102784603 A | * | 11/2012 |
| CN | 103521140 A | * | 1/2014 |

(Continued)

OTHER PUBLICATIONS

International Search Report dated Mar. 17, 2022, received in a corresponding foreign application, 8 pages.

*Primary Examiner* — Jennifer A Leung
(74) *Attorney, Agent, or Firm* — Scully Scott Murphy & Presser

(57) ABSTRACT

An ethylene oxide (EO) reactor is provided in which a removable impingement basket is configured to be inserted into the reactor inlet pipe of the EO reactor. The removable impingement basket provides protection for the silver-based catalyst filled tubes and other components that are present inside the EO reactor as well as providing another access point into the EO reactor. The removable impingement basket also can provide better distribution of the inlet gas as compared to an EO reactor containing a non-removable impingement plate.

20 Claims, 5 Drawing Sheets

(56) References Cited

U.S. PATENT DOCUMENTS

| | | | |
|---|---|---|---|
| 3,702,259 A | | 11/1972 | Nielsen |
| 4,761,394 A | | 8/1988 | Lauritzen |
| 4,766,105 A | | 8/1988 | Lauritzen |
| 4,908,343 A | | 3/1990 | Bhasin |
| 4,938,422 A | * | 7/1990 | Koves ............... B01J 8/0278 239/553.5 |
| 5,011,807 A | | 4/1991 | Hayden et al. |
| 5,057,481 A | | 10/1991 | Bhasin |
| 5,099,041 A | | 3/1992 | Hayden et al. |
| 5,102,848 A | | 4/1992 | Soo et al. |
| 5,187,140 A | | 2/1993 | Thorsteinson et al. |
| 5,407,888 A | | 4/1995 | Herzog et al. |
| 2002/0106316 A1 | * | 8/2002 | Billig ............... C07D 301/10 422/198 |
| 2003/0175183 A1 | | 9/2003 | Guetlhuber |
| 2005/0019235 A1 | | 1/2005 | McAllister et al. |
| 2007/0037991 A1 | | 2/2007 | Rizkalla |
| 2010/0032570 A1 | | 2/2010 | Tate et al. |
| 2011/0118487 A1 | | 5/2011 | Abdallah et al. |
| 2017/0232415 A1 | | 8/2017 | Gray |

FOREIGN PATENT DOCUMENTS

| | | | | |
|---|---|---|---|---|
| CN | 107115827 A | * | 9/2017 | ............ B01J 8/06 |
| DE | 102004036696 A1 | * | 2/2005 | ......... B01J 19/249 |
| GB | 721412 A | * | 1/1955 | |
| WO | 02063230 A1 | | 8/2002 | |

* cited by examiner

REMOVABLE IMPINGEMENT BASKET FOR ETHYLENE OXIDE (EO) REACTORS

FIELD OF THE INVENTION

The present invention relates to a shell-and-tube heat exchange reactor, and more particularly to an ethylene oxide reactor (EO) that contains an extra access point present at the top of the reactor.

BACKGROUND

Ethylene oxide (EO) is an important industrial chemical used as a feedstock for making various chemicals, such as, for example, ethylene glycol, ethylene glycol ethers, ethanol amines and detergents. One method for producing EO is by a catalytic oxidation process in which ethylene is reacted with oxygen in the presence of a silver-based epoxidation catalyst. In such a process, a feedstream containing ethylene and oxygen is passed over a bed of the silver-based epoxidation catalyst contained within a reaction zone of an EO reactor that is maintained at certain reaction conditions.

Commercial EO reactors are generally in the form of a shell-and-tube heat exchanger, in which a plurality of substantially parallel elongated, relatively narrow tubes are filled with catalyst particles to form a packed bed, and in which the shell contains a coolant. One such EO reactor is shown in FIG. 1. The EO reactor 1 shown in FIG. 1 includes a plurality of elongated tubes 2 in which an inlet end of each of the elongated tubes 2 is affixed to inlet tube sheet 3 and the outlet end of each of the elongated tubes 2 is affixed to outlet tube sheet 4. An inlet reactor head 5 is provided as is an exit reactor head 6.

EO reactor 1 further includes a shell and tube heat exchanger 7 that is affixed to and is integral with the exit head 6. An opening is provided in the exit head 6 for communication with heat exchanger 7, and the heat exchanger 7 is welded to the exit head 6 around the opening thus forming an integral structure with the reactor. Heat exchanger 7 is provided with tubes 8 which are affixed to tube sheets 9 and 10. Heat exchanger exit head 11 is also provided.

In practice, reaction gases, e.g., ethylene, oxygen and ballast gas are introduced into the EO reactor 1 via line 12 and pass at reaction conditions through tubes 2 which are packed with an appropriate silver-based epoxidation catalyst. Heat of reaction is removed by circulating heat transfer fluids such as water which are introduced via line 13 to the shell side of the EO reactor 1 and removed via line 14.

Reaction gases pass through tubes 2 where production of EO takes place and upon exiting tubes 2 the gases pass to exit head 6 and then to tubes 8 of the heat exchanger 7 and are immediately cooled to prevent further oxidation and isomerization. A cooling fluid, such as, for example, water, is introduced to the shell side heat exchanger 7 via line 15 and removed via line 16. Cooled reaction gases exit heat exchanger 7 via line 17 and are treated in a conventional fashion for recovery of product and recycle of various components.

Impingement plates or rods are an essential part of an EO reactor design. Impingement plates or rods prevent direct impact on flow of internal reactor components and also improve flow distribution. Typically, and as is shown in FIG. 2, an impingement plate 20 is provided at the tube side inlet of an EO reactor; FIG. 2 is an enlarged view of the upper portion of an EO reactor such as is shown in FIG. 1. The impingement plate 20 is welded to the internal surface 21 of the reactor dome and thus it is non-removable. In FIG. 2, element 22 is an inlet pipe (similar to line 12 shown in FIG. 1), element 23 is an inlet pipe flange, element 24 is an inlet tube sheet and element 26 are elongated tubes that contain a silver-based epoxidation catalyst.

As also shown in FIG. 2, the EO reactor contains two man-ways (i.e., access points) 30 for maintenance and catalyst loading/unloading at the top dome. These access points (i.e., man-ways 30) allow for inserting equipment into the reactor itself. There is a demand for an additional access point at the top of an EO reactor to ease the access and increase the safety in case of any incident inside the top confined space of the EO reactor.

SUMMARY

An ethylene oxide (EO) reactor, particularly of the shell-and-tube heat exchange type, is provided in which a removable impingement basket is configured to be inserted into the reactor inlet pipe of the EO reactor. The removable impingement basket provides protection for the silver-based catalyst filled tubes and other components that are present inside the EO reactor as well as providing another access point into the EO reactor. The removable impingement basket also can provide better (i.e., improved) distribution of the inlet gas as compared to an EO reactor containing a non-removable impingement plate.

In one aspect of the present application, an ethylene oxide (EO) reactor is provided. In one embodiment, the EO reactor includes a removable impingement basket located at an upper portion of the EO reactor and affixed to inlet pipe flanges of an inlet pipe of the EO reactor. In accordance with the present invention, the removable impingement basket includes a non-perforated hollowed-wall section having an upper end and a lower end, a mounting flange located adjacent to the upper end of the non-perforated hollowed-wall section, and a perforated hollowed-wall section located at the lower end of the non-perforated hollowed-wall section, wherein the perforated hollowed-wall section contains a plurality of through-holes configured to permit inlet gas to flow from the inlet pipe into the upper portion of the EO reactor.

DETAILED DESCRIPTION

Figure 1:
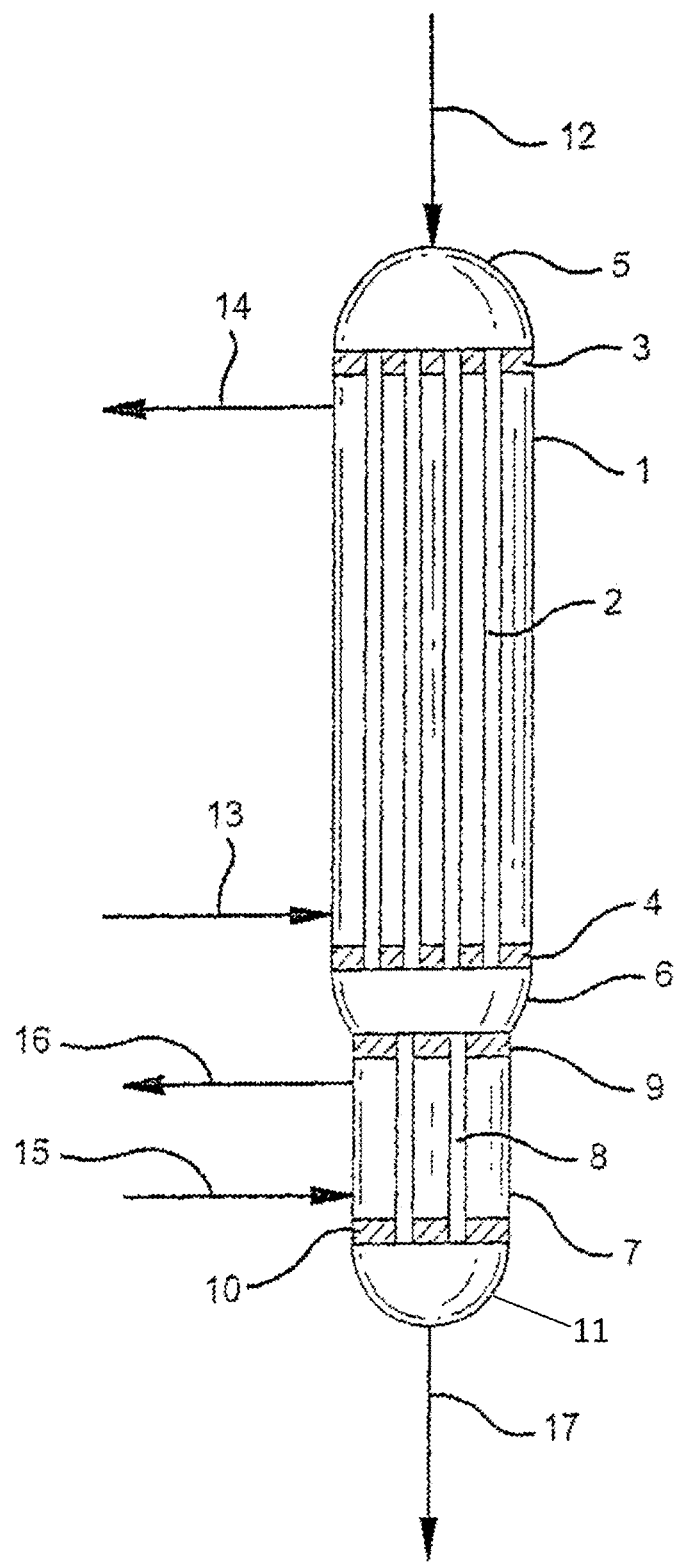
FIG. 1 is schematic representation of a prior art EO reactor.

The present invention will now be described in greater detail by referring to the following discussion and drawings that accompany the present application. It is noted that the drawings of the present invention are provided for illustrative purposes only and, as such, the drawings are not drawn to scale. It is also noted that like and corresponding elements are referred to by like reference numerals.

In the following description, numerous specific details are set forth, such as particular structures, components, materials, dimensions, processing steps and techniques, in order to provide an understanding of the various embodiments of the present invention. However, it will be appreciated by one of ordinary skill in the art that the various embodiments of the present invention may be practiced without these specific details. In other instances, well-known components or processing steps have not been described in detail in order to avoid obscuring the present invention.

The present invention provides a removable impingement basket for a shell-and-tube heat exchange type EO reactor. The removable impingement basket is configured to be inserted into the reactor inlet pipe of the EO reactor. The removable impingement basket provides protection for the silver-based catalyst filled tubes and other components that are present inside the EO reactor as well as providing another access point into the EO reactor. The removable impingement basket also can provide better distribution of the inlet gas as compared to an EO reactor containing a non-removable impingement plate. These and other aspect of the present invention will now be described in greater detail.

Figure 3:
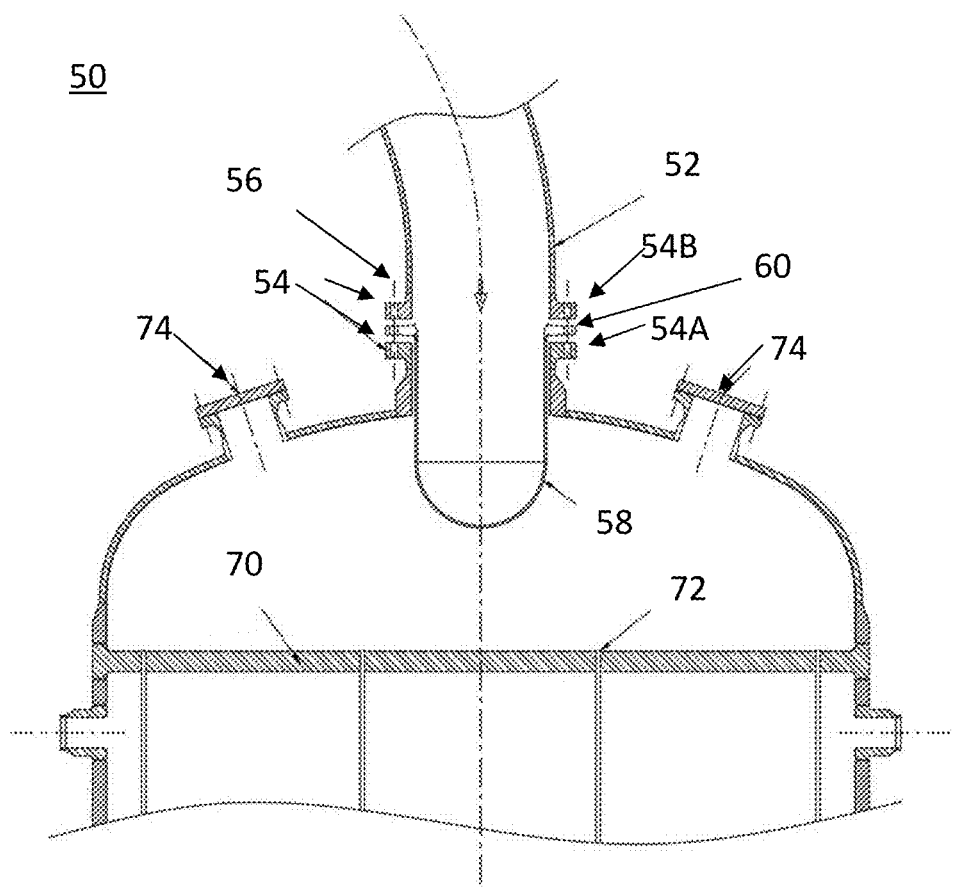
FIG. 3 is a schematic representation of an upper portion of an EO reactor including a removable impingement basket in accordance with an embodiment of the present invention.

Reference is first made to FIG. 3 which is an illustration of an upper portion of an EO reactor 50 that includes a removable impingement basket 58 (in accordance with the present invention) inserted into the inlet pipe flanges 54 of the inlet pipe 52; the lower portion of the EO reactor 50 would be similar to that shown in FIG. 1. The EO reactor 50 is a shell-and-tube heat exchange reactor similar to the one illustrated in FIG. 1. In addition to including the removable impingement basket 58 and the reactor inlet pipe 52, the EO reactor 50 shown in FIG. 3 further includes two access points 74 (a third access point can be provided when the removable impingement basket 58 is removed from the EO reactor 50), an inlet tube sheet 70 and a plurality of elongated tubes 72.

In some embodiments, access points 74 have a size from about 45 cm to about 61 cm; the term "about" when used in conjugation with a numerical value denotes that the numerical value may fluctuate from ±10% from the given numerical value. The third access point that can be provided when the removable impingement basket 58 is removed from the EO reactor 50 has a size from about 61 cm to about 163 cm. The presence of this third access point provided when the removable impingement basket 58 is removed from the EO reactor 50 is important for EO operational safety and easy access.

As known to those skilled in the art, the inlet tube sheet 70 is used to support each of the elongated tubes 72 that are present in the EO reactor 50. Each elongated tube 72 that is present in the EO reactor 50 is filled with (i.e., packed with) a silver-based epoxidation catalyst (to be defined herein below). The packing of the elongated tubes 72 with the silver-based epoxidation catalyst can be performed utilizing techniques well known to those skilled in the art. The dimensions including the inner tube diameter, outer tube diameter, and tube length, of each elongated tube 72 can vary depending on the reactor design, and such dimensional values are well known to those skilled in the art.

Figure 4:
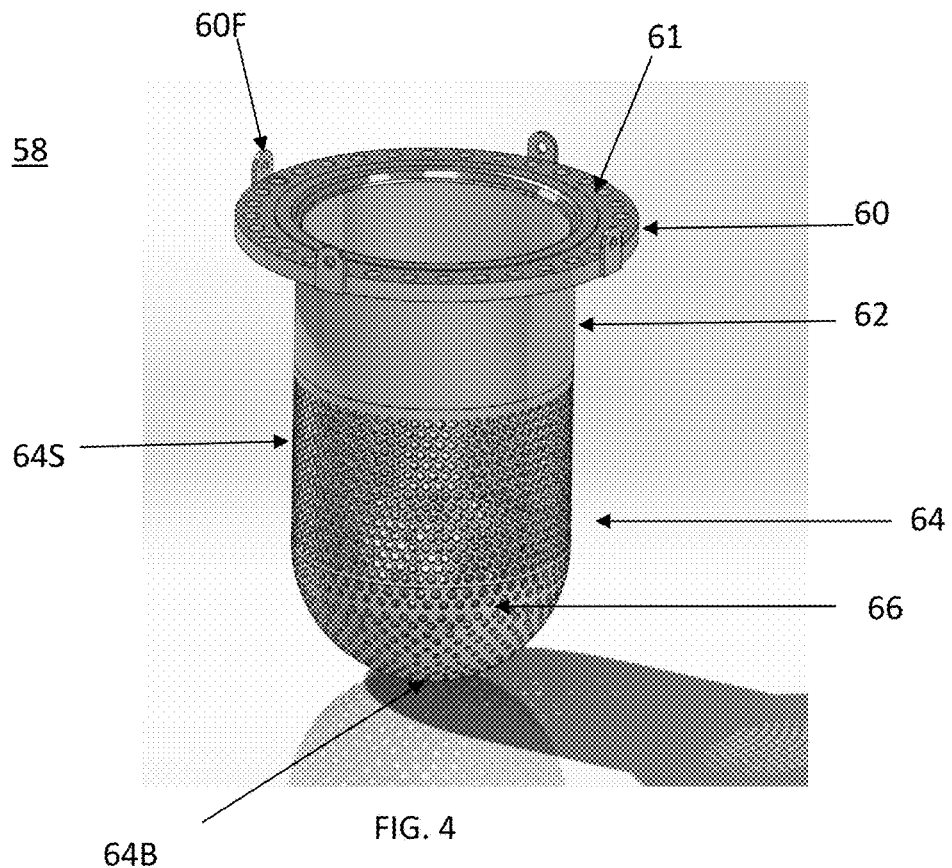
FIG. 4 is a schematic three-dimensional (3D) representation of a removable impingement basket in accordance with a first embodiment of the present invention.
Figure 5:
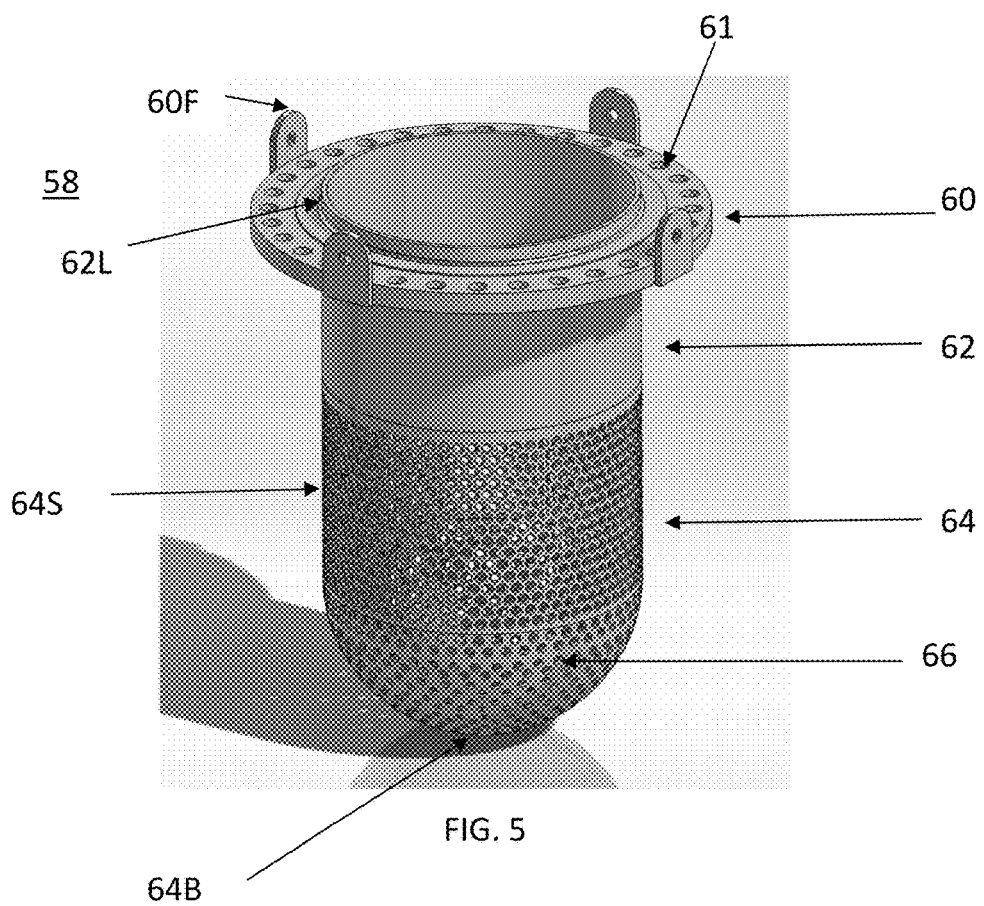
FIG. 5 is a schematic three-dimensional (3D) representation of another removable impingement basket in accordance with a second embodiment of the present invention.

As is shown in FIG. 3, the removable impingement basket 58 is located inside an upper portion of the EO reactor 50, and the removable impingement basket 58 is affixed to inlet pipe flanges 54 of the inlet pipe 52 of the EO reactor 50. As is shown in FIGS. 4 and 5, the removable impingement basket 58 of the present invention that can be present in EO reactor 50 includes a non-perforated hollowed-wall section 62 (i.e., a section whose outerwall(s) does not contain any through-holes present therein) having an upper end and a lower end, a mounting flange 60 located adjacent to the upper end of the non-perforated hollowed-wall section 62, and a perforated hollowed-wall section 64 located at the lower end of the non-perforated hollowed-wall section 62. The non-perforated hollowed-wall section 62 and perforated hollowed-wall section 64 are in communication with each other. The term "hollowed-wall section" denotes a portion of the removable impingement basket 58 in which a space for allowing feed gas flow is present between inner walls of that portion of the removable impingement basket 58.

In accordance with the present invention, the perforated hollowed-wall section 64 of the removable impingement basket 58 contains a plurality of through-holes 66 that are configured to permit inlet gas to flow from the inlet pipe 52 into the upper portion of the EO reactor 50. The term "through-holes" denotes openings which extend entirely through a material (or structure).

Each of the through-holes 66 can have a diameter from about 0.6 cm to about 8 cm; although other diameters for the through-holes 66 are possible and can be employed in the present invention so long as the diameter of the through-holes 66 is sufficiently small enough to prevent solid objects such as tools and unwanted solid particles from passing from the inlet pipe 52 into the EO reactor 50. The pitch between each of the through-holes 66, as measured from a central point of one of the through-holes to the exact same central point of a neighboring through-hole, can be from about 0.9 cm to about 11 cm; although other pitches are possible and can be used in the present invention.

In some embodiments of the present invention (See, for example FIGS. 4 and 5), the non-perforated hollowed-wall section 62, the perforated hollowed-wall section 64, and the mounting flange 60 of the removable impingement basket 58 are cylindrical. The shape of the non-perforated hollowed-wall section 62, the perforated hollowed-wall section 64, and the mounting flange 60 of the removable impingement basket 58 is however not limited to a cylindrical design; other design shapes are possible and can be used for the non-perforated hollowed-wall section 62, the perforated hollowed-wall section 64, and the mounting flange 60 of the removable impingement basket 58. In the cylindrical design shown in FIGS. 4 and 5 of the present invention, the perforated hollowed-wall section 64 can include a cylindrical outer wall 64S and a convex bottom wall 64B; the cylindrical outer wall 64S and the convex bottom wall 64B both have through-holes 66 present therein.

In some embodiments of the present invention, at least the non-perforated hollowed-wall section 62 and the perforated hollowed-wall section 64 of the removable impingement basket 58 are of integral construction (i.e., they are made from a single work piece). In such an embodiment, the mounting flange 60 can be made from a work piece that differs from the work piece that provides the non-perforated hollowed-wall section 62 and the perforated hollowed-wall section 64 of the removable impingement basket 58. In such an embodiment, the mounting flange 60 can be affixed at the upper end of the non-perforated hollowed-wall section 62 using solder or other affixing means. In other embodiments of the present invention, the non-perforated hollowed-wall section 62, the perforated hollowed-wall section 64 and the mounting flange 60 of the removable impingement basket 58 are all of integral construction. The removable impingement basket 58 can be formed utilizing techniques well known to those skilled in the art. For example, cold/hot forming/rolling machines like hydraulic press or roller as well as drilling/cutting/welding machines can be used to form the removable impingement basket 58.

The removable impingement basket 58 including the non-perforated hollowed-wall section 62, the perforated hollowed-wall section 64 and the mounting flange 60 can be composed of a material(s) that is(are) well known to those skilled in the art. In one example, the removable impingement basket 58 including the non-perforated hollowed-wall section 62, the perforated hollowed-wall section 64 and the mounting flange 60 can be composed of stainless steel.

In some embodiments of the present invention, and as is shown in FIG. 4, the mounting flange 60 has a surface that is flush with a topmost surface of the upper end of the non-perforated hollowed-wall section 62. In other embodiments of the present invention, and as is shown in FIG. 5, the mounting flange 60 has a surface that is located beneath a topmost surface of the upper end of the non-perforated hollowed-wall section 62. In such an embodiment, the mounting flange 60 can be formed adjacent to an outer wall of the non-perforated hollowed-wall section 62. Also and in such an embodiment, a lip section 62L (such as is shown in FIG. 5) of the non-perforated hollowed-wall section 62 is exposed and this lip section 62L can be welded directly to the inlet pipe 52.

In accordance with an embodiment of the present invention and as is shown in FIG. 3, the inlet pipe flanges 54 include a plurality of top inlet pipe flanges 54B and bottom inlet pipe flanges 54A that are affixed to the outer wall of the inlet pipe 52 of the EO reactor 50. Each top inlet pipe flange 54B is paired with one of the bottom pipe inlet flanges 54A to provide a paired inlet pipe flange set 54A/54B. In some embodiments (not specifically illustrated), the top inlet pipe flanges 54BA can be omitted and only bottom inlet pipe flanges 54A are present.

In accordance with an embodiment of the present invention and when the removable impingement basket shown in FIG. 4 is used, the mounting flange 60 is sandwiched between the top inlet pipe flanges 54B and the bottom inlet pipe flanges 54A (See, FIG. 3). In accordance with another embodiment of the present invention and when the removable impingement basket shown in FIG. 5 is used, a portion of the mounting flange 60 is positioned atop each bottom inlet pipe flanges 54A; the portion of the mounting flange 60 that is seated atop the bottom inlet pipe flanges 54A is a surface of the mounting flange that contains through-holes 61.

As is further shown in FIGS. 4-5, the mounting flange 60 has a surface containing a plurality of through-holes 61 present therein. In some embodiments and when the removable impingement basket shown in FIG. 4 is used, each through-hole 61 present in the surface of the mounting flange 60 is configured to align with through-holes (not specifically labeled) present in each paired inlet pipe flange set (54A/54B). As is illustrated in FIG. 3, a single stud bolt 56 is positioned in each through-hole present in the surface of the mounting flange 60 and the through-holes present in each paired inlet pipe flange set (54A/54B). In other embodiments and when the removable impingement basket shown in FIG. 5 is used, each through-hole 61 present in the surface of the mounting flange 60 is configured to align with through-holes (not specifically labeled) present in the bottom inlet pipe flanges 54A. In such an embodiment, a single stud bolt is positioned in each through-hole present in the surface of the mounting flange 60 and the through-holes present the bottom inlet pipe flanges 54A.

In accordance with an embodiment of the present invention and as is shown in FIGS. 4 and 5, the mounting flange 60 contains a plurality of lifting fingers (or lugs) 60F (four are shown by way of one example in FIGS. 4-5) extending upward from an outer wall of the surface of the mounting flange 60 that contains through-holes 61. The presence of the lifting fingers 60 aids in lifting the removable impingement basket 58 from the EO reactor 50 once the EO reactor 50 is shut down and stud bolts 56 have been removed. The presence of the lifting fingers 60F also aids in inserting the removable impingement basket 58 into inlet pipe 52 of the EO reactor 50.

Figure 6:
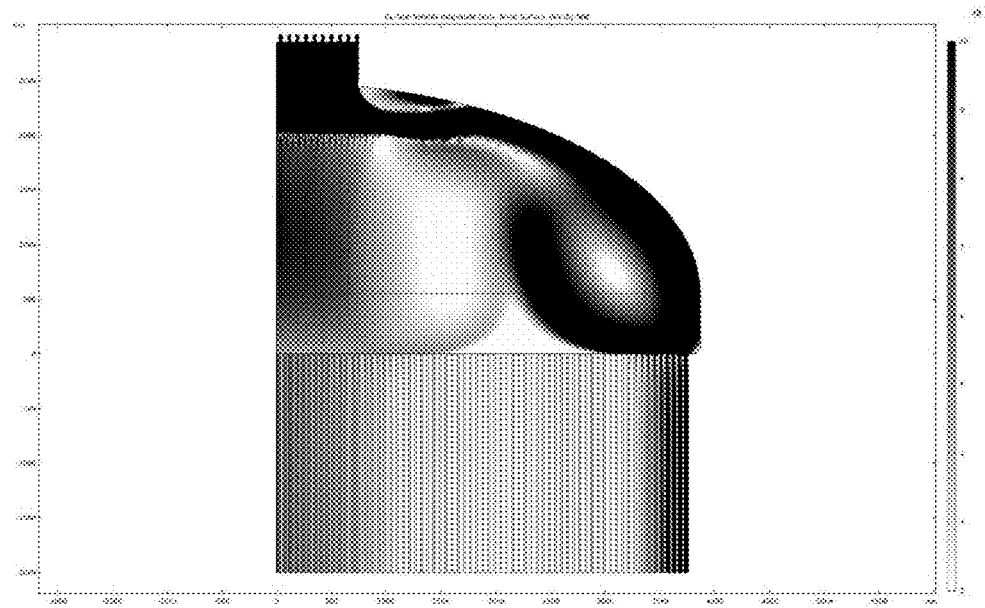
FIG. 6 is a schematic representation of gas velocity/distribution using a conventional, non-removable impingement plate.
Figure 7:
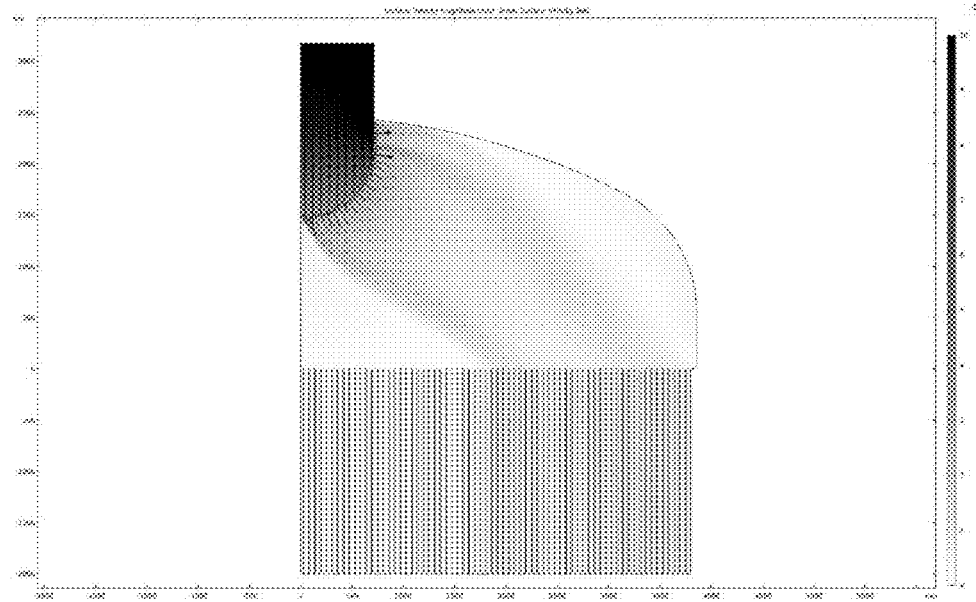
FIG. 7 is schematic representation of gas velocity/distribution using a removable impingement basket in accordance with the present invention.

Referring now to FIGS. 6 and 7, there are shown schematic representations of gas velocity/distributions using a conventional, non-removable impingement plate (FIGS. 2 and 6), and using a removable impingement basket (FIGS. 3 and 7) in accordance with the present invention. As is shown, the presence of the removable impingement basket of the present invention (See, FIG. 7) provides better distribution of the inlet gas as compared to an EO reactor containing a non-removable impingement plate (See, FIG. 6).

Figure 2:
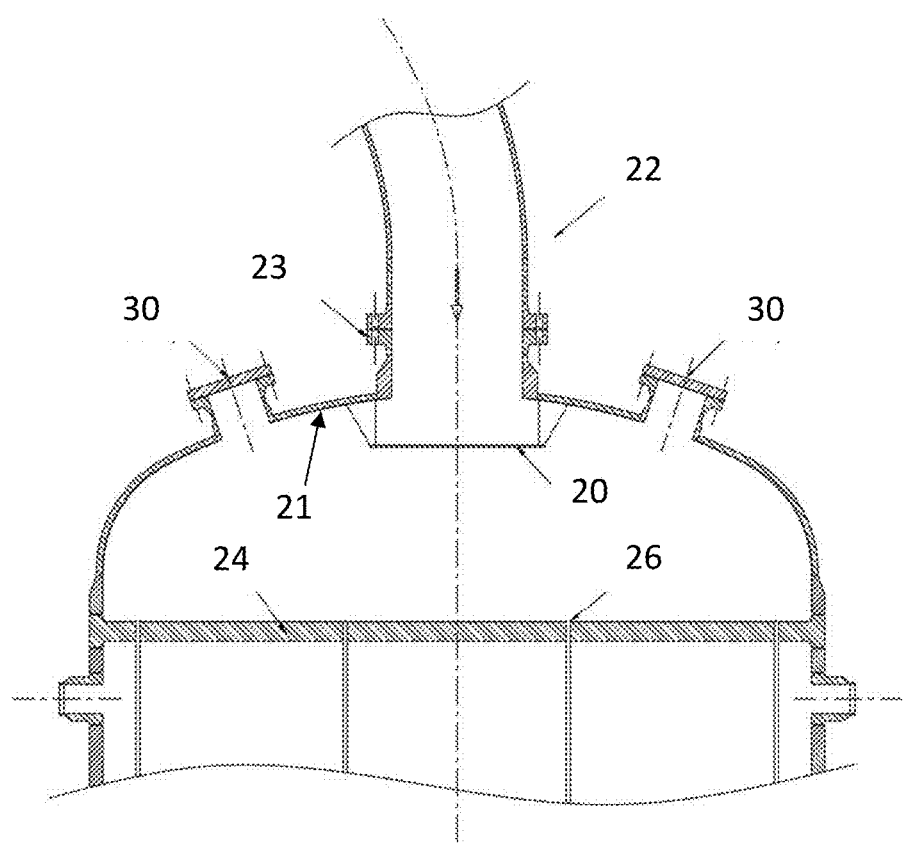
FIG. 2 is a schematic representation of an upper portion of a prior art EO reactor including a conventional, non-removable, impingement plate.

As shown in FIG. 6, inlet gas impinges the permanent impingement plate 20 of FIG. 2 and gets diverted to the sides which are fully open. This makes the steam flow upward into the internal surface 21 of the reactor dome of FIG. 2 and follow its curvature. Any carryover particle will hit the internal surface 21 of the reactor dome and may get into peripheral elongated tubes 26 of FIG. 2. Also the gas distribution is uneven inside to chamber 5 of FIG. 1. In the example shown in FIG. 7, which uses a removal impingement basket of the present invention, inlet gas will be evenly distributed at the top EO chamber 5 of FIG. 1. No large particle will escape from the removal impingement basket and those which remain removal impingement basket can be collected during plant shutdown.

The description that follows provides some details regarding the silver-based epoxidation catalyst that can be present inside the EO reactor 50 and some details regarding the EO operational conditions used during EO manufacturing. The description below is not meant to be exhaustive but provides a general description of both the silver-based epoxidation catalyst and EO operational conditions that can be used in the present invention.

Typical silver-based epoxidation catalysts include a support, and at least a catalytically effective amount of silver or a silver-containing compound; also optionally present is a promoting amount of rhenium or a rhenium-containing compound; also optionally present is a promoting amount of one or more alkali metals or alkali-metal-containing compounds. The support employed can be selected from a large number of solid, refractory supports that may be porous and may provide the preferred pore structure. Alumina is well known to be useful as a catalyst support for the epoxidation of an olefin and is a preferred support for silver-based epoxidation catalysts.

Regardless of the character of the support used, it is usually shaped into particles, chunks, pieces, pellets, rings, spheres, wagon wheels, cross-partitioned hollow cylinders, and the like, of a size suitable for employment in a fixed-bed epoxidation reactor. The support particles will preferably have equivalent diameters in the range from about 3 mm to about 12 mm, and more preferably in the range from about 5 mm to about 10 mm. (Equivalent diameter is the diameter of a sphere having the same external surface (i.e., neglecting surface within the pores of the particle) to volume ratio as the support particles being employed.) Suitable supports are available from Saint-Gobain Norpro Co., Sud Chemie AG, Noritake Co., CeramTec AG, and Industrie Bitossi S.p.A. Without being limited to the specific compositions and formulations contained therein, further information on support compositions and methods for making supports may be found in U.S. Patent Publication No. 2007/0037991.

In order to produce a catalyst for the oxidation of an olefin to an olefin oxide, a support having the above characteristics is then provided with a catalytically effective amount of silver on its surface. In one embodiment, the catalytic effective amount of silver is from 10% by weight to 45% by weight. The catalyst can be prepared by impregnating the support with a silver compound, complex or salt dissolved in a suitable solvent sufficient to cause deposition of a silver-precursor compound onto the support. Preferably, an aqueous silver solution can be used.

A promoting amount of a rhenium component, which may be a rhenium-containing compound or a rhenium-containing complex may also be deposited on the support, either prior to, coincidentally with, or subsequent to the deposition of the silver. The rhenium promoter may be present in an amount from about 0.001 wt. % to about 1 wt. %, preferably from about 0.005 wt. % to about 0.5 wt. %, and more preferably from about 0.01 wt. % to about 0.1 wt. % based on the weight of the total catalyst including the support, expressed as the rhenium metal.

Other components which may also be deposited on the support either prior to, coincidentally with, or subsequent to the deposition of the silver and rhenium are promoting amounts of an alkali metal or mixtures of two or more alkali metals, as well as optional promoting amounts of a Group IIA alkaline earth metal component or mixtures of two or more Group IIA alkaline earth metal components, and/or a transition metal component or mixtures of two or more transition metal components, all of which may be in the form of metal ions, metal compounds, metal complexes and/or metal salts dissolved in an appropriate solvent. The support may be impregnated at the same time or in separate steps with the various catalyst promoters. The particular combination of support, silver, alkali metal promoter(s), rhenium component, and optional additional promoter(s) of the instant invention will provide an improvement in one or more catalytic properties over the same combination of silver and support and none, or only one of the promoters.

As used herein the term "promoting amount" of a certain component of the catalyst refers to an amount of that component that works effectively to improve the catalytic performance of the catalyst when compared to a catalyst that does not contain that component. The exact concentrations employed, of course, will depend on, among other factors, the desired silver content, the nature of the support, the viscosity of the liquid, and solubility of the particular compound used to deliver the promoter into the impregnating solution. Examples of catalytic properties include, inter alia, operability (resistance to runaway), selectivity, activity, conversion, stability and yield. It is understood by one skilled in the art that one or more of the individual catalytic properties may be enhanced by the "promoting amount" while other catalytic properties may or may not be enhanced or may even be diminished.

Suitable alkali metal promoters may be selected from lithium, sodium, potassium, rubidium, cesium or combinations thereof, with cesium being preferred, and combinations of cesium with other alkali metals being especially preferred. The amount of alkali metal deposited or present on the support is to be a promoting amount. Preferably, the amount ranges from about 10 ppm to about 3000 ppm, more preferably from about 15 ppm to about 2000 ppm, and even more preferably from about 20 ppm to about 1500 ppm, and as especially preferred from about 50 ppm to about 1000 ppm by weight of the total catalyst, measured as the metal.

Suitable alkaline earth metal promoters comprise elements from Group IIA of the Periodic Table of the Elements, which may be beryllium, magnesium, calcium, strontium, and barium or combinations thereof. Suitable transition metal promoters may comprise elements from Groups IVA, VA, VIA, VIIA and VIIIA of the Periodic Table of the Elements, and combinations thereof.

The amount of alkaline earth metal promoter(s) and/or transition metal promoter(s) deposited on the support is a promoting amount. The transition metal promoter may typically be present in an amount from about 0.1 micromoles per gram to about 10 micromoles per gram, preferably from about 0.2 micromoles per gram to about 5 micromoles per gram.

The silver solution used to impregnate the support may also comprise an optional solvent or a complexing/solubilizing agent such as are known in the art. A wide variety of solvents or complexing/solubilizing agents may be employed to solubilize silver to the desired concentration in the impregnating medium. Useful complexing/solubilizing agents include amines, ammonia, oxalic acid, lactic acid and combinations thereof. Amines include an alkylene diamine having from 1 to 5 carbon atoms. In one preferred embodiment, the solution comprises an aqueous solution of silver oxalate and ethylene diamine. The complexing/solubilizing agent may be present in the impregnating solution in an amount from about 0.1 to about 5.0 moles per mole of silver, preferably from about 0.2 to about 4.0 moles, and more preferably from about 0.3 to about 3.0 moles for each mole of silver.

When a solvent is used, it may be an organic solvent or water, and may be polar or substantially or totally non-polar. In general, the solvent should have sufficient solvating power to solubilize the solution components. At the same time, it is preferred that the solvent be chosen to avoid having an undue influence on or interaction with the solvated promoters. Organic-based solvents which have 1 to about 8 carbon atoms per molecule are preferred. Mixtures of several organic solvents or mixtures of organic solvent(s) with water may be used, provided that such mixed solvents function as desired herein.

The concentration of silver in the impregnating solution is typically in the range from about 0.1% by weight up to the maximum solubility afforded by the particular solvent/solubilizing agent combination employed. It is generally very suitable to employ solutions containing from 0.5% to about 45% by weight of silver, with concentrations from 5 to 35% by weight of silver being preferred.

Impregnation of the selected support is achieved using any of the conventional methods; for example, excess solution impregnation, incipient wetness impregnation, spray coating, etc. Typically, the support material is placed in contact with the silver-containing solution until a sufficient amount of the solution is absorbed by the support. Preferably the quantity of the silver-containing solution used to impregnate the porous support is no more than is necessary to fill the pores of the support. A single impregnation or a series of impregnations, with or without intermediate drying, may be used, depending, in part, on the concentration of the silver component in the solution. Impregnation procedures are described, for example, in U.S. Pat. Nos. 4,761,394, 4,766,105, 4,908,343, 5,057,481, 5,187,140, 5,102,848, 5,011,807, 5,099,041 and 5,407,888. Known prior procedures of pre-deposition, co-deposition and post-deposition of various the promoters can be employed.

After impregnation of the support with the silver-containing compound, i.e., a silver precursor, optional rhenium component, an optional alkali metal component, and the optional other promoters, the impregnated support is calcined for a time sufficient to convert the silver containing compound to an active silver species and to remove the volatile components from the impregnated support to result in a catalyst precursor. The calcination may be accomplished by heating the impregnated support, preferably at a gradual rate, to a temperature in the range from about 200° C. to about 600° C. at a pressure in the range from about 0.5 to about 35 bar. In general, the higher the temperature, the shorter the required heating period. A wide range of heating periods have been suggested in the art; e.g., U.S. Pat. No. 3,563,914 discloses heating for less than 300 seconds, and U.S. Pat. No. 3,702,259 discloses heating from 2 to 8 hours at a temperature of from 100° C. to 375° C., usually for duration of from about 0.5 to about 8 hours. However, it is only important that the heating time be correlated with the temperature such that substantially all of the contained silver is converted to the active silver species. Continuous or step-wise heating may be used for this purpose.

During calcination, the impregnated support may be exposed to a gas atmosphere comprising an inert gas or a mixture of an inert gas with from about 10 ppm to 21% by volume of an oxygen-containing oxidizing component. For purposes of this invention, an inert gas is defined as a gas that does not substantially react with the catalyst or catalyst precursor under the conditions chosen for the calcination. Further information on catalyst manufacture may be found in the aforementioned U.S. Patent Publication No. 2007/0037991.

For purposes of illustration only, the following are conditions that are often used in current commercial EO reactor units: a gas hourly space velocity (GHSV) of 1500-10,000 $h^{-1}$, a reactor inlet pressure of 1 Mpa to 3 MPa, a coolant temperature of 180-315° C., an oxygen conversion level of 10-60%, and an EO production rate (work rate) of 100-350 kg EO/m$^3$ catalyst/hr and a change in ethylene oxide concentration, $\Delta$EO, of from about 1.5% to about 4.5%. The feed composition in the reactor inlet after the completion of start-up and during normal operation typically comprises (by volume %) 1-40% ethylene, 3-12% $O_2$; 0.2% to 10%, preferably 0.2% to 6%, more preferably 0.2% to 5% of $CO_2$; 0-5% ethane, an amount of one or more chloride moderators, which are described herein; and the balance of the feed being comprised of argon, methane, nitrogen or mixtures thereof.

While the present invention has been particularly shown and described with respect to preferred embodiments thereof, it will be understood by those skilled in the art that the foregoing and other changes in forms and details may be made without departing from the spirit and scope of the present invention. It is therefore intended that the present invention not be limited to the exact forms and details described and illustrated, but fall within the scope of the appended claims.

What is claimed is:

1. An ethylene oxide (EO) reactor comprising:
a removable impingement basket located at an upper portion of the EO reactor and affixed to inlet pipe flanges of an inlet pipe of the EO reactor, wherein the removable impingement basket comprises a non-perforated hollowed-wall section having an upper end and a lower end, a mounting flange located adjacent to the upper end of the non-perforated hollowed-wall section, and a perforated hollowed-wall section located at the lower end of the non-perforated hollowed-wall section, wherein the perforated hollowed-wall section contains a plurality of through-holes configured to permit inlet gas to flow from the inlet pipe into the upper portion of the EO reactor, and the mounting flange comprises a plurality of lifting fingers extending upward from a surface thereof.

2. The EO reactor of claim 1, wherein the non-perforated hollowed-wall section, the perforated hollowed-wall section, and the mounting flange are cylindrical.

3. The EO reactor of claim 2, wherein the perforated hollowed-wall section comprises a cylindrical outer wall and a convex bottom wall.

4. The EO reactor of claim 1, wherein at least the non-perforated hollowed-wall section and the perforated hollowed-wall section are of integral construction.

5. The EO reactor of claim 1, wherein the mounting flange has a surface that is flush with a topmost surface of the upper end of the non-perforated hollowed-wall section.

6. The EO reactor of claim 1, wherein the mounting flange has a surface that is located beneath a topmost surface of the upper end of the non-perforated hollowed-wall section.

7. The EO reactor of claim 1, wherein the inlet pipe flanges comprise a plurality of top inlet pipe flanges and bottom inlet pipe flanges affixed to an outer wall of the inlet pipe of the EO reactor, wherein each top inlet pipe flange is paired with one of the bottom inlet pipe flanges to provide a paired inlet pipe flange set.

8. The EO reactor of claim 7, wherein the mounting flange is sandwiched between the top inlet pipe flanges and the bottom inlet pipe flanges.

9. The EO reactor of claim 8, wherein the mounting flange has a surface containing a plurality of through holes, wherein each through-hole present in the surface of the mounting flange is configured to align with through-holes present in each paired inlet pipe flange set.

10. The EO reactor of claim 9, wherein a single stud bolt is positioned in each of the through-holes present in the surface of the mounting flange and each through-holes present in each paired inlet pipe flange set.

11. The EO reactor of claim 1, wherein the inlet pipe flanges comprise a plurality of bottom inlet pipe flanges affixed to an outer wall of the inlet pipe of the EO reactor.

12. The EO reactor of claim 11, wherein the mounting flange has a surface containing a plurality of through holes, wherein the surface of the mounting flange containing the plurality of through-holes is seated atop each of the bottom inlet pipe flanges and wherein each through-hole present in the surface of the mounting flange is configured to align with through-holes present in each of the bottom inlet pipe flanges.

13. The EO reactor of claim 12, wherein a single stud bolt is positioned in each of the through-holes present in the surface of the mounting flange and each through-holes present in each of the bottom inlet pipe flanges.

14. The EO reactor of claim 1, wherein the EO reactor is a shell-and-tube heat exchange reactor.

15. The EO reactor of claim 1, further comprising a plurality of elongated tubes located in the EO reactor and positioned beneath the removable impingement basket.

16. The EO reactor of claim 15, wherein each elongated tube is filled with a silver-based epoxidation catalyst comprising an alumina support and at least a catalytically effective amount of silver or a silver-containing compound.

17. The EO reactor of claim 16, wherein the silver-based epoxidation catalyst comprises an alumina support and at least a catalytically effective amount of silver or a silver-containing compound.

18. An ethylene oxide (EO) reactor comprising:
a removable impingement basket located at an upper portion of the EO reactor and affixed to inlet pipe flanges of an inlet pipe of the EO reactor, wherein the removable impingement basket comprises a non-perforated hollowed-wall section having an upper end and a lower end, a mounting flange located adjacent to the upper end of the non-perforated hollowed-wall section, and a perforated hollowed-wall section located at the lower end of the non-perforated hollowed-wall section, wherein the perforated hollowed-wall section contains a plurality of through-holes configured to permit inlet gas to flow from the inlet pipe into the upper portion of the EO reactor, and wherein the mounting flange has a surface that is located beneath a topmost surface of the upper end of the non-perforated hollowed-wall section.

19. An ethylene oxide (EO) reactor comprising:
a removable impingement basket located at an upper portion of the EO reactor and affixed to inlet pipe flanges of an inlet pipe of the EO reactor, wherein the removable impingement basket comprises a non-perforated hollowed-wall section having an upper end and a lower end, a mounting flange located adjacent to the upper end of the non-perforated hollowed-wall section, and a perforated hollowed-wall section located at the lower end of the non-perforated hollowed-wall section, wherein the perforated hollowed-wall section contains a plurality of through-holes configured to permit inlet gas to flow from the inlet pipe into the upper portion of the EO reactor, the inlet pipe flanges comprise a plurality of top inlet pipe flanges and bottom inlet pipe flanges affixed to an outer wall of the inlet pipe of the EO reactor, each top inlet pipe flange is paired with one of the bottom inlet pipe flanges to provide a paired inlet pipe flange set, the mounting flange is sandwiched between the top inlet pipe flanges and the bottom inlet pipe flanges, and the mounting flange has a surface containing a plurality of through holes, and wherein each through-hole present in the surface of the mounting flange is configured to align with through-holes present in each paired inlet pipe flange set.

20. An ethylene oxide (EO) reactor comprising:
a removable impingement basket located at an upper portion of the EO reactor and affixed to inlet pipe flanges of an inlet pipe of the EO reactor, wherein the removable impingement basket comprises a non-perforated hollowed-wall section having an upper end and a lower end, a mounting flange located adjacent to the upper end of the non-perforated hollowed-wall section, and a perforated hollowed-wall section located at the lower end of the non-perforated hollowed-wall section, wherein the perforated hollowed-wall section contains a plurality of through-holes configured to permit inlet gas to flow from the inlet pipe into the upper portion of the EO reactor, the inlet pipe flanges comprise a plurality of bottom inlet pipe flanges affixed to an outer wall of the inlet pipe of the EO reactor, and the mounting flange has a surface containing a plurality of through holes, and wherein the surface of the mounting flange containing the plurality of through-holes is seated atop each of the bottom inlet pipe flanges and wherein each through-hole present in the surface of the mounting flange is configured to align with through-holes present in each of the bottom inlet pipe flanges.

\* \* \* \* \*